United States Patent
West et al.

(10) Patent No.: US 10,481,167 B2
(45) Date of Patent: Nov. 19, 2019

(54) METHODS FOR MEASURING CONCENTRATIONS OF BIOMOLECULES

(75) Inventors: Tim West, Saint Louis, MO (US); Andrew Corey Paoletti, Saint Louis, MO (US)

(73) Assignee: C2N Diagnostics, Saint Louis, MO (US)

( * ) Notice: Subject to any disclaimer, the term of this patent is extended or adjusted under 35 U.S.C. 154(b) by 0 days.

(21) Appl. No.: 13/132,307

(22) PCT Filed: Dec. 4, 2009

(86) PCT No.: PCT/US2009/066810
§ 371 (c)(1),
(2), (4) Date: Sep. 23, 2011

(87) PCT Pub. No.: WO2010/065878
PCT Pub. Date: Jun. 10, 2010

(65) Prior Publication Data
US 2012/0015371 A1  Jan. 19, 2012

Related U.S. Application Data

(60) Provisional application No. 61/120,326, filed on Dec. 5, 2008, provisional application No. 61/120,329, filed on Dec. 5, 2008.

(51) Int. Cl.
| G01N 33/68 | (2006.01) |
| G01N 33/537 | (2006.01) |
| G01N 33/58 | (2006.01) |

(52) U.S. Cl.
CPC ....... *G01N 33/6896* (2013.01); *G01N 33/537* (2013.01); *G01N 33/58* (2013.01); *G01N 33/6848* (2013.01); *G01N 2458/15* (2013.01); *G01N 2496/00* (2013.01); *G01N 2800/28* (2013.01); *G01N 2800/2821* (2013.01)

(58) Field of Classification Search
CPC .............. G01N 33/58; G01N 33/6896; G01N 2800/28–304; G01N 2458/15
See application file for complete search history.

(56) References Cited

U.S. PATENT DOCUMENTS

| 5,741,713 | A | 4/1998 | Brown et al. |
| 7,396,654 | B2 | 7/2008 | Hayes et al. |
| 7,449,171 | B2 | 11/2008 | Hellerstein |
| 7,892,845 | B2 | 2/2011 | Bateman |
| 8,084,016 | B2 | 12/2011 | Hellerstein |
| 9,464,122 | B2 | 10/2016 | Moe |
| 2003/0228259 | A1 | 12/2003 | Hellerstein |
| 2004/0096907 | A1 | 5/2004 | Bohrmann et al. |
| 2004/0229283 | A1 | 11/2004 | Gygi |
| 2005/0003375 | A1 | 1/2005 | Franze et al. |
| 2007/0134802 | A1 | 6/2007 | Doebeli |
| 2008/0145941 | A1 | 6/2008 | Bateman |
| 2008/0171317 | A1 | 7/2008 | Deiters et al. |
| 2008/0206737 | A1 | 8/2008 | Hunter |
| 2008/0220449 | A1 | 9/2008 | Vasan et al. |
| 2008/0286814 | A1 | 11/2008 | Lopez |
| 2010/0169988 | A1 | 7/2010 | Kohli et al. |
| 2011/0202000 | A1 | 8/2011 | Benz et al. |
| 2011/0312059 | A1 | 12/2011 | Moe |
| 2012/0015371 | A1 | 1/2012 | West |
| 2012/0029169 | A1 | 2/2012 | Moe |
| 2016/0313353 | A1 | 10/2016 | West |
| 2017/0015717 | A1 | 1/2017 | Moe |

FOREIGN PATENT DOCUMENTS

| EP | 1 420 254 A2 | 5/2004 |
| EP | 1 686 372 A1 | 8/2006 |
| WO | WO 2000/055187 A1 | 9/2000 |
| WO | WO 03/068919 A2 | 8/2003 |
| WO | WO 2003/068919 A2 | 8/2003 |
| WO | WO 2005059556 A1 * | 6/2005 |
| WO | WO 2006/017812 A1 | 2/2006 |
| WO | WO 2006/107814 A2 | 10/2006 |
| WO | WO 2008/145763 A1 | 12/2008 |
| WO | WO 2010/021755 A2 | 2/2010 |
| WO | WO 2010/065878 A1 | 6/2010 |

OTHER PUBLICATIONS

Kuhn E et al. (2004) Quantification of C-reactive protein in the serum of patients with rheumatoid arthritis using multiple reaction monitoring mass spectrometry and 13C-labeled peptide standards. Proteomics, 4:1175-1186.*
Mayya V & Han DK. Proteomic applications of protein quantification by isotope-dilution mass spectrometry. Expert Rev. Proteomics, 2006, 3(6):597-610.*
Nakamura T & Oda Y (2007) Mass spectrometry-based quantitative proteomics. Biotechnol. Genetic Engineering Rev. 24:147-164.*
Gelfanova V et al. (2007) Quantitative analysis of amyloid-beta peptides in cerebrospinal fluid using immunoprecipitation and MALDI-Tof mass spectrometry. Briefings in Functional Genomics & Proteomics, 6(2):149-158.*
Oe T et al. (2006) Quantitative analysis of amyloid beta peptides in cerebrospinal fluid of Alzheimer's disease patients by immunoaffinity purification and stable isotope dilution liquid chromatography/ negative electrospray ionization tandem mass spectrometry. Rapid Commun. Mass Spectrom. 20:3273-3735.*
Duncan MW et al. (Sep. 2008) Quantitative matrix-assisted laser desorption/ionization mass spectrometry. Brief Funct. Genomic. Proteomic.7(5):355-370.*

(Continued)

*Primary Examiner* — Kimberly Ballard
(74) *Attorney, Agent, or Firm* — DLA Piper LLP (US)

(57) ABSTRACT

The present invention provides methods for measuring the absolute concentration of a biomolecule of interest in a subject. Such biomolecules may be implicated in one or more neurological and neurodegenerative diseases or disorders. Also provided is a method for determining whether a therapeutic agent affects the in vivo metabolism of a central nervous system derived biomolecule. Also provided are kits for performing the methods of the invention.

17 Claims, 4 Drawing Sheets

Specification includes a Sequence Listing.

(56) References Cited

OTHER PUBLICATIONS

Quadroni, M. Protein separation and sample preparation for mass spectrometry, Lausanne Protein Analysis Facility, 31 pages. Retrieved online from: embnet.vital-it.ch/CoursEMBnet/PROT04/Slides/Prot_sep%26sample_prepMS.pdf on Jun. 18, 2019. (Year: 1996).*
McClintock and Shaw, "A Novel S100 Target Conformation is Revealed by the Solution Structure of the $Ca^{2+}$-S100B-TRTK-12 Complex," *J. Biol. Chem.* (2003), 278(8):6251-6257, The American Society for Biochemistry and Molecular Biology, Inc.
Rüfenacht et al., "Quantification of the A beta peptide in Alzheimer's plaques by laser dissection microscopy combined with mass spectrometry", *J. Mass Spectrom.*, 40(2):193-201 (2005).
International Search Report (ISR) from PCT/US2012/67110.
Communication from European Patent Office in application No. EP 09 831 209.3.
Bereszczak, Jessica Z. et al.: "*Relative Quantification of Tau-related Peptides Using Guanidino-labeling Derivatization (GLaD) with Online-LC on a Hybrid Ion Trap (IT) Time-of-Flight (ToF) Mass Spectrometer*"; J Am Soc Mass Spectrom, 2007, 18, p. 201-207.
Extended European Search Report dated May 19, 2015, regarding EP 12 85 4345.
European Examination Report dated Jan. 22, 2013, regarding EP 09 831 209.3.
Extended European Search Report dated May 14, 2012, regarding EP 09 831 209.3.
European Search Report dated Mar. 27, 2015, regarding EP 15 155 419.
Extended European Search Report dated May 19, 2015, regarding EP 12 854 345.1.
International Search Report dated Feb. 15, 2013, regarding PCT/US2012/067110.
Japanese Office Action dated Aug. 22, 2016, regarding JP 2014-544889.
European Examination Report dated Jan. 17, 2017, regading EP 12 854 345.1.
Kito et al.: "*Mass Spectrometry-Based Approaches Toward Absolute Quntitative Proteomics*"; Current Genomics, vol. 9:4, 2008, pp. 263-274.
Adams et al.: "*Three Repeat Isoforms of Tau Inhibit Assembly of Four Repeat Tau Filaments*"; PLoS ONE, May 2010, vol. 5, Issue 5, pp. 1-9, e10810.
Leblond et al.: "*Preclinical Whole-body Fluorescence Imaging: Review of Instruments, Methods and Applications*"; J Photochem Photobiol B., Jan. 21, 2010,98(1): 77-94.
Andreadis, Athena: "*Tau gene alternative splicing: expression patterns, regulation and modulation of function in normal brain and neurodegenerative diseases*"; Biochimica et Biophysica Acta 2005; 1739:91-103.
Baldwin, Michael A.: "*Protein Identification by Mass Spectrometry: issues to be considered*"; Molecular & Cellular Proteomics 3.1, Jan. 1, 2004, published on Nov. 6, 2003, 3 (1) 1-9; doi.org/10.1074/mcp.R300012-MCP200.
Castellani, Rudy J. et al.: "*Tau Biology, Tauopathy, Traumatic Brain Injury, and Diagnostic Challenges*"; J. Alzheimer's Disease; 2019; 67:447-467. DOI 10.3233/JAD-180721.
Espindola, Sonia Lorena et al.: "*Modulation of Tau Isoforms Imbalance Precludes Tau Pathology and Cognitive Decline in a Mouse Model of Tauopathy*"; Cell Reports, 2018; 23:709-715.
Merriam-Webster Dictionary: "*The Definition of in vivo*"; retrieved from the online website on Mar. 31, 2019, pp. 1-8.
Miller, Philip W. et al.: "*Synthesis of $^{11}C, ^{18}F, ^{15}O$ and $^{15}N$ Radiolabels for Positron Emission Tomography*"; Angew. Chem. Int. Ed., 2008; 47:8998-9033.
Park, Sun Ah et al.: "*Tau mis-splicing in the pathogenesis of neurodegenerative disorders*"; BMB Rep., 2016; 49:405-413.

* cited by examiner

METHODS FOR MEASURING CONCENTRATIONS OF BIOMOLECULES

CROSS REFERENCE TO RELATED APPLICATIONS

This application is a 35 USC § 371 National Stage application of International Application No. PCT/US2009/066810 filed Dec. 4, 2009, now pending; which claims the benefit under 35 USC § 119(e) to U.S. Application Ser. No. 61/120,329 filed Dec. 5, 2008, and to U.S. Application Ser. No. 61/120,326 filed Dec. 5, 2008. The disclosure of each of the prior applications is considered part of and is incorporated by reference in the disclosure of this application.

BACKGROUND OF THE INVENTION

Field of the Invention

The invention generally relates to methods for the diagnosis and treatment of neurological and neurodegenerative diseases, disorders, and associated processes.

Background Information

Alzheimer's Disease (AD) is the most common cause of dementia and is an increasing public health problem. It is currently estimated to afflict 5 million people in the United States, with an expected increase to 13 million by the year 2050 (Herbert et al, 2001, *Alzheimer Dis. Assoc. Disord.* 15(4): 169-173). AD, like other central nervous system (CNS) degenerative diseases, is characterized by disturbances in protein production, accumulation, and clearance. In AD, dysregulation in the metabolism of the protein, amyloid-beta (Aβ), is indicated by a massive buildup of this protein in the brains of those with the disease. AD leads to loss of memory, cognitive function, and ultimately independence and death. The disease takes a heavy personal and financial toll on the patient, the family, and society. Because of the severity and increasing prevalence of this disease in the population, it is urgent that better treatments be developed.

Currently, there are some medications that modify symptoms, however, there are no disease-modifying treatments. Disease-modifying treatments will likely be most effective when given before the onset of irreversible brain damage. However, by the time clinical diagnosis of AD is made, extensive neuronal loss has already occurred (Price et al. 2001, *Arch. Neurol.* 58(9): 1395-1402). Therefore, a way to identify those at risk of developing AD would be most helpful in preventing or delaying the onset of AD. Currently, there are no means of identifying the pathophysiologic changes that occur in AD before the onset of clinical symptoms or of effectively measuring the effects of treatments that may prevent the onset or slow the progression of the disease.

A need therefore exists for a sensitive, accurate, and reproducible method for quantifying biomolecules in a subject. Previous technologies used for absolute quantitation include enzyme linked immunosorbent assays (ELISAs), which use antibodies to capture and measure the concentrations. However, ELISAs quantitate total concentration or rely on isoform specific antibodies for quantitation and can, for the most part, be used to measure the concentration of only one species per assay. Antibodies are highly specific for the protein species and the conformations of the proteins they bind and the reliance upon two antibodies binding to the protein of interest can lead to high inter- and intra-assay variability in the reported concentrations from ELISA assays. As such, a method is needed for measuring the absolute quantitation of the concentrations of one or more biomolecules in biological fluids and tissues in vivo, where the biomolecules are associated with the diagnosis and/or progression of diseases.

SUMMARY OF THE INVENTION

Among the various aspects of the present invention is the provision of a method for calculating the concentration of one or more biomolecules in a subject. The method includes contacting a sample from the subject with a Quantitation Standard, where the Quantitation Standard is a known concentration of a labeled biomolecule of interest. The method further includes isolating the biomolecule of interest from the sample and determining a ratio of labeled to unlabeled biomolecules in the sample, which is thereby used to calculate the concentration of the unlabeled biomolecule in the sample. In one embodiment, the method further includes normalizing the calculated concentration to a standard curve, wherein the standard curve is generated by determining two or more ratios of unlabeled biomolecules to Quantitation Standard, where the concentration of the unlabeled biomolecule is known.

In another aspect, the present invention provides an in vivo method of quantifying the concentration of one or more biomolecules in a subject. The method includes administering one or more labeled amino acids to the subject, where the labeled amino acids incorporate into a biomolecule of interest in the subject. The method further includes obtaining a sample of biological fluid or tissue from the subject, where the sample includes a labeled biomolecule fraction and an unlabeled biomolecule fraction. The sample is then contacted with a Quantitation Standard, where the Quantitation Standard includes a known concentration of a biomolecule labeled with a moiety that has a molecular weight that differs from the one or more labeled amino acids administered to the subject. The ratio of labeled biomolecule to the Quantitation Standard and the ratio of unlabeled biomolecule to the Quantitation Standard can then be used to calculate the concentrations of both labeled and unlabeled biomolecules, respectively. In one embodiment, calculating the concentration of the unlabeled biomolecule comprises multiplying the concentration of the Quantitation Standard with the determined ratio of unlabeled biomolecule to the Quantitation Standard. In another embodiment, calculating the concentration of the labeled biomolecule comprises multiplying the concentration of the Quantitation Standard with the determined ratio of labeled biomolecule to the Quantitation Standard. In yet another embodiment, the calculated concentrations of unlabeled and labeled biomolecules are normalized to each their individual standard curves, wherein the standard curve is generated by determining two or more ratios of unlabeled and labeled biomolecules to Quantitation Standard, where the concentration of unlabeled and labeled biomolecule is known.

In another aspect, the invention provides a method for measuring the in vivo metabolism of one or more biomolecules produced in the central nervous system of a subject. The method comprises administering a labeled moiety to the subject, wherein the labeled moiety is capable of crossing the blood brain barrier and incorporating into the biomolecule(s) as the one or more biomolecules is produced in the central nervous system of the subject. The method further comprises obtaining a central nervous system sample from the subject, wherein the central nervous system sample is a central nervous system tissue or fluid. The central nervous system sample comprises a labeled biomolecule fraction in which the labeled moiety is incorporated into the one or more biomolecules, and an unlabeled biomolecule fraction in which the labeled moiety is not incorporated into the one or more biomolecules. The final step of the process comprises detecting the amount of labeled biomolecule and the amount of unlabeled biomolecule for each of the one or more biomolecules, wherein the ratio of labeled biomolecule to unlabeled biomolecule for each biomolecule is directly proportional to the metabolism of said biomolecule in the subject.

In another aspect, the invention provides a method for determining whether a therapeutic agent affects the metabolism of a biomolecule produced in the central nervous system of a subject. The method comprises administering a therapeutic agent and a labeled moiety to the subject, wherein the labeled moiety is capable of crossing the blood brain barrier and incorporating into the biomolecule as it is being is produced in the central nervous system of the subject. The method further comprises obtaining a biological sample from the subject, wherein the biological sample comprises a labeled biomolecule fraction in which the labeled moiety is incorporated into the biomolecule, and an unlabeled biomolecule fraction in which the labeled moiety is not incorporated into the biomolecule. The next step of the process comprises detecting the amount of labeled biomolecule and the amount of unlabeled biomolecule, wherein the ratio of labeled biomolecule to unlabeled biomolecule is directly proportional to the metabolism of the biomolecule in the subject. The final step of the process comprises comparing the metabolism of the biomolecule in the subject to a suitable control value, wherein a change from the control value indicates the therapeutic agent affects the metabolism of the biomolecule in the central nervous system of the subject.

In another aspect, the invention provides a kit for performing the methods of the invention. In one embodiment, a kit is provided for diagnosing and/or monitoring the progression or treatment of a neurological or neurodegenerative disease in a subject. The kit includes one or more labeled moieties (e.g., labeled amino acids) and a means for administering the one or more amino acids to the subject. The kit may further include a means for obtaining a biological sample at regular time intervals from the subject. In certain embodiments, the kit will also include instructions for detecting and determining the ratio of labeled to unlabeled biomolecules of interest over time and for calculating the concentration of the unlabeled biomolecule. In one embodiment, the instructions will disclose methods for comparing the calculated concentration to certain standards and/or controls as disclosed herein.

In all aspects, the labeled moiety includes a non-radioactive isotope that is selected from the group consisting of $^{2}H$, $^{13}C$, $^{15}N$, $^{17}O$, $^{18}O$, $^{33}S$, $^{34}S$, and $^{36}S$. In one embodiment, the labeled moiety is a labeled amino acid, such as an essential amino acid. Exemplary essential amino acids include, but are not limited to leucine, isoleucine, and phenylalanine. Thus, in one embodiment, the labeled moiety is $^{13}C_x$-leucine, where x=1 to 6. In another embodiment, the labeled moiety is a $^{15}N$-labeled amino acid. In another embodiment, the labeled moiety is a $^{13}C_x$-labeled phenylalanine, where x=1 to 9. In another embodiment, the labeled moiety is a $^{13}C_x$-labeled isoleucine, where x=1 to 6. In another embodiment, the labeled moiety is a $^{13}C_x$-labeled isoleucine and a $^{13}C_y$-labeled phenylalanine, where x=1 to 6, and y=1 to 9.

In all aspects, the biomolecule may be a peptide, lipid, nucleic acid, or carbohydrate. In one embodiment, the biomolecule is a peptide that is synthesized in the central nervous system (CNS) such as amyloid-beta (Aβ), alpha-synuclein, Tau, apolipoprotein E, apolipoprotein J, amyloid precursor protein (APP), alpha-2-macroglobulin, S100B, myelin basic protein, TDP-43, superoxide dismutase-1, huntingtin, an interleukin, and TNF. In aspects of the invention where two or more biomolecules are assayed, the biomolecules may be isoforms of the same protein. As such, in one embodiment, the biomolecule may be one or more of Aβ 1-16, Aβ 1-17, Aβ 1-37, Aβ 1-38, Aβ 1-39, Aβ 1-40, Aβ 1-41, Aβ 1-42, and Aβ 1-43.

Other aspects and features of the invention are described in more detail below.

DETAILED DESCRIPTION OF THE INVENTION

Figure 1:
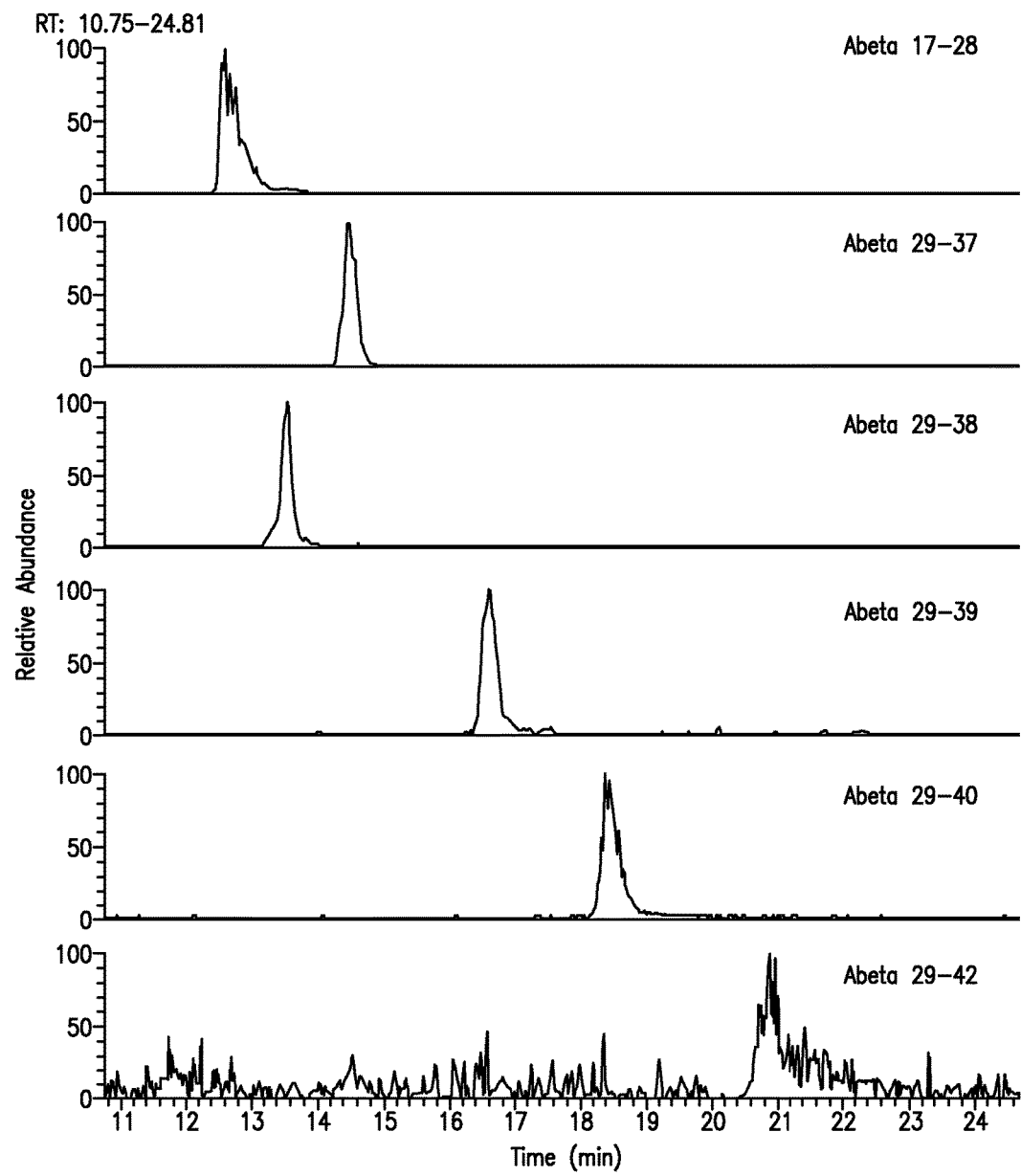
FIG. 1 is a graphical representation showing the results of chromatography of the different tryptic Aβ (Abeta) peptides isolated from cell culture media showing the peaks of Aβ 17-28, Aβ 29-37, Aβ 29-38, Aβ 29-39, Aβ 29-40 and Aβ 29-42.

The present invention is based, in part, on the discovery that stable isotope labeling of biomolecules leads to small differences in molecular weight of the biomolecules, but does not alter the physical or chemical properties of the biomolecules. Using the techniques provided herein, analysis of biomolecules can be used to diagnose and/or treat a subject having or at risk of developing a neurological or neurodegenerative disorder. Accordingly, the present invention provides methods and kits useful for calculating the concentration of one or more biomolecules of interest in a subject.

The invention also provides a method to assess whether a therapeutic agent affects the production or clearance rate of biomolecules in the subject, where the biomolecules are relevant to neurological or neurodegenerative diseases. Accordingly, the method may be used to determine the optimal doses and/or optimal dosing regimes of the therapeutic agent. Additionally, the method may be used to determine which subjects respond better to a particular therapeutic agent. For example, subjects with increased production of the biomolecule may respond better to one therapeutic agent, whereas subjects with decreased clearance of the biomolecule may respond better to another therapeutic agent. Alternatively, subjects with one particular genotype may respond better to a particular therapeutic agent than those with a different genotype. Finally, by allowing isoform specific quantitation, the method may be used to determine whether a therapeutic agent can modulate the production of a biomolecule by switching production of one isoform to another isoform of the same biomolecule.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In addition, the term "subject" may refer to a culture of cells, where the methods of the invention are performed in vitro to assess, for example, efficacy of a therapeutic agent.

As used herein, the terms "sample" and "biological sample" refer to any sample suitable for the methods provided by the present invention. A sample of cells used in the present method can be obtained from tissue samples or bodily fluid from a subject, or tissue obtained by a biopsy procedure (e.g., a needle biopsy) or a surgical procedure. In certain embodiments, the biological sample of the present invention is a sample of bodily fluid, e.g., cerebral spinal fluid (CSF), blood, plasma, urine, saliva, and tears.

As disclosed herein, stable isotope labeling of biomolecules leads to small differences in molecular weight of the biomolecules, but does not alter the physical or chemical properties of the biomolecules. Thus, the biomolecules will bind to antibodies and elute off a liquid chromatography column in an identical fashion. Sensitive instruments, such as mass spectrometers, provide the ability to measure small differences in weight between labeled and unlabeled biomolecules.

Accordingly, in one aspect, the invention provides a method of calculating the concentration of a biomolecule in a subject. In one embodiment, the method includes contacting a sample from the subject with a Quantitation Standard. As used herein, a "Quantitation Standard" refers to a known concentration of a labeled biomolecule, which has a distinct molecular weight from other labeled or unlabeled biomolecules that may exist in the sample. Thereafter, a sensitive measuring device, such as a mass spectrometer, a tandem mass spectrometer, or a combination of both, is used to measure the ratio of labeled to unlabeled biomolecules. Since the physical properties of the labeled and unlabeled biomolecules are identical, the ratio measured by the mass spectrometer is identical to the ratio in the original sample. Thus, by adding a known amount of one or more biomolecules, each labeled with a unique isotopic label, the invention provides the ability to quantitate the amount of those biomolecules that have different isotopic composition.

As used herein, the term "biomolecule" refers to any organic molecule in a living organism. Exemplary biomolecules include, but are not limited to, peptides, lipids, nucleic acids, and carbohydrates. In one embodiment, the biomolecule is a peptide, such as a protein, that is synthesized in the central nervous system (CNS) of the subject. Exemplary proteins that can be measured by the methods of the invention include, but are not limited to, amyloid-β (Aβ) and its variants, soluble amyloid precursor protein (APP), apolipoprotein E (isoforms 2, 3, or 4), apolipoprotein J (also called clusterin), Tau (associated with Alzheimer's Disease), phospho Tau, glial fibrillary acidic protein, alpha-2 macroglobulin, alpha-synuclein, S100B, myelin basic protein (implicated in multiple sclerosis), prions, interleukins, TDP-43, superoxide dismutase-1, huntingtin, tumor necrosis factor (TNF), heat shock protein 90 (HSP90), and combinations thereof. Additional biomolecules that may be targeted include products of, or proteins or peptides that interact with, GABAergic neurons, noradrenergic neurons, histaminergic neurons, seratonergic neurons, dopaminergic neurons, cholinergic neurons, and glutaminergic neurons. In one embodiment, the protein whose in vivo concentration is measured may be an apolipoprotein E protein. In another embodiment, the protein whose in vivo concentration is measured may be alpha-synuclein. In another embodiment, the protein whose in vivo concentration is measured may be Aβ or its variants or isoforms. Exemplary isoforms of Aβ whose concentrations may be measured include, but are not limited to, Aβ 1-16, Aβ 1-17, Aβ 1-37, Aβ 1-38, Aβ 1-39, Aβ 1-40, Aβ 1-41, Aβ 1-42, and Aβ 1-43.

By way of example and not limitation, it is noted that several C-terminally unique isoforms of Aβ exist in CSF. Trypsin digestion of these peptides yields a 29-x peptide which is unique to each isoform, see Table 1. Thus, quantitation of the 29-x isoform allows for calculation of the concentration of these isoforms in the original biological fluid.

TABLE 1

Location of the trypsin cleavage sites in the major isoforms of Aβ. The C-terminal peptides (29-x, GAII . . . ) are the peptides that differ between the different isoforms.

| | | | |
|---|---|---|---|
| Aβ 37 | DAEFR_HDSGYEVHHQK_LVFFAEDVGSNK_GAIIGLMVG | SEQ ID NO: | 1 |
| Aβ 38 | DAEFR_HDSGYEVHHQK_LVFFAEDVGSNK_GAIIGLMVGG | SEQ ID NO: | 2 |
| Aβ 39 | DAEFR_HDSGYEVHHQK_LVFFAEDVGSNK_GAIIGLMVGGV | SEQ ID NO: | 3 |
| Aβ 40 | DAEFR_HDSGYEVHHQK_LVFFAEDVGSNK_GAIIGLMVGGVV | SEQ ID NO: | 4 |
| Aβ 42 | DAEFR_HDSGYEVHHQK_LVFFAEDVGSNK_GAIIGLMVGGVVIA | SEQ ID NO: | 5 |

As such, the methods provide the ability to measure concentrations of fragments of various isoforms of Aβ, such as fragments produced after digestion with an endoprotease (e.g., trypsin or V8 protease). Exemplary fragments of Aβ isoforms include, but are not limited to N-terminal peptide fragments (e.g., Aβ 1-5, Aβ 1-16), mid-domain fragments (e.g., Aβ 17-28) and C-terminal peptide fragments (e.g., 29-x peptides, such as Aβ 29-37, Aβ 29-38, Aβ 29-39, Aβ 29-40, and Aβ 29-42).

As used herein, the term "nucleic acid" refers to DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

The terms "polypeptide," "peptide" and "protein" are used interchangeably herein to refer to two or more amino acid residues joined to each other by peptide bonds or modified peptide bonds, i.e., peptide isosteres. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. "Polypeptide" refers to both short chains, commonly referred to as peptides, oligopeptides or oligomers, and to longer chains, generally referred to as proteins. Polypeptides may contain amino acids other than the 20 gene-encoded amino acids. Likewise, "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration.

Several different moieties may be used to label the biomolecule of interest. Generally speaking, the two types of labeling moieties utilized in the method of the invention are radioactive isotopes and non-radioactive (stable) isotopes. In one embodiment, non-radioactive isotopes may be used and measured by mass spectrometry. Preferred stable isotopes include deuterium ($^2$H), $^{13}$C, $^{15}$N, $^{17}$ or $^{18}$O, and $^{33, 34,}$ or $^{36}$S, but it is recognized that a number of other stable isotopes that change the mass of an atom by more or less neutrons than is seen in the prevalent native form would also be effective. A suitable label generally will change the mass of the biomolecule under study such that it can be detected in a mass spectrometer. In one embodiment, the biomolecule to be measured may be a peptide or protein, and the labeled moiety may be an amino acid comprising a non-radioactive isotope (e.g., $^{13}$C). In another embodiment, the biomolecule to be measured may be a nucleic acid, and the labeled moiety may be a nucleoside triphosphate comprising a non-radioactive isotope (e.g., $^{15}$N). Alternatively, a radioactive isotope may be used, and the labeled biomolecules may be measured with a scintillation counter (or via nuclear scintigraphy) as well as by a mass spectrometer. One or more labeled moieties may be used simultaneously or in sequence.

Thus, in one embodiment, when the method is employed to measure the concentration of proteins, the labeled moiety typically will be an amino acid. Those of skill in the art will appreciate that several amino acids may be used to provide the label of biomolecules. Generally, the choice of amino acid is based on a variety of factors such as: (1) The amino acid generally is present in at least one residue of the protein or peptide of interest. (2) The amino acid is generally able to quickly reach the site of protein production and rapidly equilibrate across the blood-brain barrier or other tissue or cellular barriers. (3) The amino acid label generally does not influence the metabolism of the protein of interest (e.g., very large doses of leucine may affect muscle metabolism). And (5) availability of the desired amino acid (i.e., some amino acids are much more expensive or harder to manufacture than others).

In one embodiment, the amino acid is an essential amino acid (not produced by the body), so that a higher percent of labeling may be achieved. In another embodiment, the amino acid is a non-essential amino acid. Exemplary amino acids include, but are not limited to, leucine, isoleucine, and phenylalanine. As such, in one embodiment, the labeled amino acid is one or more of a $^{15}$N-labeled amino acid, a $^{13}$C$_x$-labeled phenylalanine, where x=1 to 9, a $^{13}$C$_x$-labeled isoleucine, where x=1 to 6. For example, $^{13}$C$_6$-phenylalanine, which contains six $^{13}$C atoms, may be used to label a biomolecule of interest (e.g., a CNS derived protein). In another embodiment, $^{13}$C$_6$-leucine may be used to label a biomolecule of interest (e.g., a CNS derived protein). In yet another embodiment, $^{13}$C$_6$-leucine is used to label A.

There are numerous commercial sources of labeled amino acids, both non-radioactive isotopes and radioactive isotopes. Generally, the labeled amino acids may be produced either biologically or synthetically. Biologically produced amino acids may be obtained from an organism (e.g., kelp/seaweed) grown in an enriched mixture of $^{13}$C, $^{15}$N, or another isotope that is incorporated into amino acids as the organism produces proteins. The amino acids are then separated and purified. Alternatively, amino acids may be made with known synthetic chemical processes.

The labeled moiety (e.g., labeled amino acid) may be administered to a subject by several methods. Suitable routes of administration include intravenously, intra-arterially, subcutaneously, intraperitoneally, intramuscularly, or orally. In one embodiment, the labeled moiety may be administered by intravenous infusion. In another embodiment, the labeled moiety may be orally ingested.

The labeled moiety may be administered slowly over a period of time, as a large single dose depending upon the type of analysis chosen (e.g., steady state or bolus/chase), or slowly over a period of time after an initial bolus dose. To achieve steady-state levels of the labeled biomolecule, the labeling time generally should be of sufficient duration so that the labeled biomolecule may be reliably quantified. In one embodiment, the labeled moiety is administered as a single oral dose. In another embodiment, the labeled moiety is administered for a period of time ranging from about one hour to about 36 hours. In another embodiment, the labeled moiety is administered for a period of time ranging from about 6 hours to about 12 hours. In yet another embodiment, the labeled moiety is administered for a period of time ranging from about 9 hours to about 12 hours. In yet another embodiment, the labeled moiety is administered for a period of time ranging from about 9 hours to about 24 hours.

The rate of administration of the labeled moiety may range from about 0.5 mg/kg/hr to about 5 mg/kg/hr. In one embodiment, the rate of administration of labeled leucine is from about 1 mg/kg/hr to about 3 mg/kg/hr. In another embodiment, the rate of administration of labeled leucine is from 1.8 mg/kg/hr to about 2.5 mg/kg/hr. In another embodiment, the labeled leucine may be administered as a bolus of between about 50 and about 500 mg/kg body weight of the subject, between about 50 and about 300 mg/kg body weight of the subject, or between about 100 and about 300 mg/kg body weight of the subject. In yet another embodiment, the labeled leucine may be administered as a bolus of about 200 mg/kg body weight of the subject. In an alternate embodiment, the labeled leucine may be administered intravenously as detailed above after an initial bolus of between about 0.5 to about 10 mg/kg, between about 1 to about 4 mg/kg, or about 2 mg/kg body weight of the subject.

Those of skill in the art will appreciate that the amount (or dose) of the labeled moiety can and will vary. Generally, the amount is dependent on (and estimated by) the following factors: (1) The type of analysis desired. For example, to achieve a steady state of about 15% labeled leucine in plasma requires about 2 mg/kg/hr over about 9 hr after an initial bolus of 2 mg/kg over 10 min. In contrast, if no steady state is required, a large bolus of labeled moiety (e.g., 1 or 5 grams of labeled leucine) may be given initially. (2) The protein under analysis. For example, if the protein is being produced rapidly, then less labeling time may be needed and less label may be needed—perhaps as little as 0.5 mg/kg over 1 hour. However, most proteins have half-lives of hours to days and, so more likely, a continuous infusion for 4, 9 or 12 hours may be used at 0.5 mg/kg to 4 mg/kg. And (3) the sensitivity of detection of the label. For example, as the sensitivity of label detection increases, the amount of label that is needed may decrease.

It should be understood that more than one labeled moiety may be used in a single subject. This would allow multiple labeling of the same biomolecule and may provide information on the production or clearance of that biomolecule at different times. For example, a first label may be given to subject over an initial time period, followed by a pharmacologic agent (drug), and then a second label may be administered. In general, analysis of the samples obtained from the subject would provide a measurement of concentrations of biomolecules of interest before AND after drug administration, directly measuring the pharmacodynamic effect of the drug in the same subject. Alternatively, multiple labels may be used at the same time to increase labeling of the biomolecule.

Thus, once disease is established and a treatment protocol is initiated, the methods of the invention may be repeated on a regular basis to monitor the concentration(s) of biomolecule(s) of interest in the subject. The results obtained from successive assays may be used to show the efficacy of treatment over a period ranging from several days to months. Accordingly, another aspect of the invention is directed to methods for monitoring a therapeutic regimen for treating a subject having a neurological or neurodegenerative disorder. A comparison of the concentration(s) of biomolecule(s) of interest prior to and during therapy will be indicative of the efficacy of the therapy. Therefore, one skilled in the art will be able to recognize and adjust the therapeutic approach as needed.

The method of the invention provides that a sample be obtained from the subject such that the in vivo concentration of one or more biomolecules of interest can be determined. In one embodiment, the sample is a body fluid. Suitable body fluids include, but are not limited to, cerebral spinal fluid (CSF), blood plasma, blood serum, urine, saliva, perspiration, and tears. It should be understood that biological fluids typically contain a multitude of quantifiable biomolecules. For example, where the sample is CSF, exemplary biomolecules that can be quantified include, but are not limited to, amyloid-beta protein, variants of amyloid-beta protein (Aβ), digestion products of amyloid-beta protein, amyloid precursor protein (APP), apolipoprotein E, apolipoprotein J, Tau, alpha-synuclein, or any combination thereof. In another embodiment, the sample is a tissue sample, such as a sample of tissue from the central nervous system (CNS). The sample generally will be collected using standard procedures well known to those of skill in the art.

In one embodiment, the sample is a CNS sample, which includes, but is not limited to, tissue from the central nervous system, which comprises brain tissue and spinal cord tissue. In one embodiment of the invention, the CNS sample may be taken from brain tissue, including, but not limited to, tissue from the forebrain (e.g., cerebral cortex, basal ganglia, hippocampus), the interbrain (e.g., thalamus, hypothalamus, subthalamus), the midbrain (e.g., tectum, tegmentum), or the hindbrain (e.g., pons, cerebellum, medulla oblongata). In another embodiment, the CNS sample may be collected from spinal cord tissue. In still other embodiments, CNS samples from more than one CNS region may be taken. Accordingly, the concentration of a biomolecule of interest may be measured in different CNS samples, e.g., in the cortex and the hippocampus, simultaneously.

CNS samples may be obtained by known techniques. For instance, brain tissue or spinal cord tissue may be obtained via dissection or resection. Alternatively, CNS samples may be obtained using laser microdissection. The subject may or may not have to be sacrificed to obtain the sample, depending on the CNS sample desired and the subject utilized.

In general when the biomolecule under study is a peptide or protein, the invention provides that a first sample may be taken from a subject prior to administration of the labeled moiety to provide a baseline. After administration of the labeled moiety (e.g., labeled amino acid), one or more samples are obtained from the subject. As will be appreciated by those of skill in the art, the number of samples and when the samples are taken generally will depend upon a number of factors such as: the type of analysis, type of administration, the protein of interest, the rate of metabolism, the type of detection, and the type of subject.

In one embodiment, the sample is obtained from the subject at a single predetermined time point, for example, within an hour of labeling. In general, for proteins with fast metabolism, samples obtained during the first 12-18 hours after the start of administration of the labeled moiety may be used to determine the rate of production of the biomolecule of interest, and samples taken during 24-36 hrs after the start of administration of the labeled moiety may be used to determine the clearance rate of the biomolecule of interest. In another embodiment, the sample is obtained from the subject hourly from 0 to 12 hours, 0 to 24 hours, or 0 to 36 hours. In yet another embodiment, samples may be taken from an hour to days or even weeks apart depending upon the production and clearance rates of the biomolecule of interest.

It should be understood that if samples at different time-points are desired, more than one subject may be used. For instance, one subject may be used for a baseline sample, another subject for a time-point of one hour post administration of the labeled moiety, another subject for a time-point six hours post administration of the labeled moiety.

Accordingly, the present invention provides that detection of the amount of labeled biomolecule and the amount of unlabeled biomolecule in the sample may be used to determine the ratio of labeled biomolecule to unlabeled biomolecule, which in turn, may be used to calculate the concentration of the biomolecule of interest in the subject. In one embodiment, the ratio is determined by means of detecting changes in mass of the labeled biomolecule (e.g., peptide or protein) with respect to the unlabeled biomolecule. Exemplary means for detecting differences in mass between the labeled and unlabeled biomolecules include, but are not limited to, liquid chromatography mass spectrometry, gas chromatography mass spectrometry, MALDI-TOF mass spectrometry, and tandem mass spectrometry.

However, prior to detecting the ratio of labeled biomolecule to unlabeled biomolecule, it may be desirable to isolate and/or separate the biomolecule of interest from other biomolecules in the sample. Thus, in one embodiment, immunoprecipitation may be used to isolate and purify the biomolecule (e.g., peptide or protein) of interest before it is analyzed. In another embodiment, the biomolecule of interest may be isolated or purified by affinity chromatography or immunoaffinity chromatography. Alternatively, mass spectrometers having chromatography setups may be used to separate biomolecules without immunoprecipitation, and then the biomolecule of interest may be measured directly. In an exemplary embodiment, the protein of interest may be immunoprecipitated and then analyzed by a liquid chromatography system interfaced with a tandem MS unit equipped with an electrospray ionization source (LC-ESI-tandem MS).

In another aspect, the invention provides that multiple biomolecules in the same sample may be measured simultaneously. That is, both the amount of unlabeled and labeled biomolecule may be detected and measured separately or at the same time for multiple biomolecules. As such, the invention provides a useful method for screening changes in production and clearance of one or more biomolecules on a large scale (i.e., proteomics/metabolomics) and provides a sensitive means to detect and measure biomolecules involved in the underlying pathophysiology. In aspect, the invention also provides a means to measure multiple types of biomolecules. In this context, for example, a protein and a lipid may be measured simultaneously or sequentially.

Once the amount of labeled and unlabeled biomolecule has been detected in a sample, the ratio or percent of labeled biomolecule to unlabeled biomolecule may be determined. Thereafter, the concentration of the unlabeled biomolecule in the sample can be determined. In other words, since a known amount of labeled biomolecule is added to an unknown amount of biomolecules and the ratio of labeled to unlabeled is measured, the concentration of the unlabeled biomolecules can be calculated from the ratio as follows:

Concentration of unlabeled=(ratio of unlabeled to labeled)×(concentration of labeled). (i)

The equation may be simplified as:

Concentration of unlabeled=(ratio of unlabeled: Quantitation Standard)×(concentration of Quantitation Standard). (ii)

Conversely, if a known amount of unlabeled is added to an unknown amount labeled the concentration of the labeled can be calculated as follows:

Concentration of labeled=(ratio of labeled to unlabeled)×(concentration of unlabeled). (iii)

In addition, if a known amount of biomolecule 1, labeled with label 1, is added to an unknown amount of biomolecule 2, labeled with label 2, the concentration of the biomolecule 2 can be calculated as follows:

Concentration of label 2=(ratio of label 2 to label 1)×(concentration of label 1). (iv)

Similarly, if a known amount of biomolecule 1, labeled with label 1, is added to an unknown amount of biomolecule 2, labeled with label 2, and biomolecule 3, labeled with label 3, the concentration of the biomolecule 2 and biomolecule 3 can be calculated as follows:

Concentration of label 2=(ratio of label 2 to label 1)×(concentration of label 1) (v)

Concentration of label 3=(ratio of label 3 to label 1)×(concentration of label 1). (vi)

Finally, if a known amount of biomolecule 1, labeled with label 1, is added to an unknown amount of biomolecule 2, labeled with label 2, and an unknown amount of unlabeled biomolecule 3, the concentration of the biomolecule 2 and unlabeled biomolecule can be calculated as follows:

Concentration of label 2=(ratio of label 2 to label 1)×(concentration of label 1) (vii)

Concentration of unlabeled=(ratio of unlabeled to label 1)×(concentration of label 1). (viii)

In another embodiment, the methods further include the step of normalizing the calculated concentration to a standard curve based on the curve fitting equation generated by the standard curve. The standard curve used herein is generated by determining two or more ratios of unlabeled biomolecules to their respective Quantitation Standards, where the concentration of the unlabeled biomolecule of interest is known.

In another aspect, the invention allows measurement of the labeled and unlabeled protein at the same time, so that the ratio of labeled to unlabeled protein, as well as other calculations, may be made. Those of skill in the art will be familiar with the first order kinetic models of labeling that may be used with the method of the invention. For example, the fractional synthesis rate (FSR) may be calculated. The FSR equals the initial rate of increase of labeled to unlabeled protein divided by the precursor enrichment. Likewise, the fractional clearance rate (FCR) may be calculated. In addition, other parameters, such as lag time and isotopic tracer steady state, may be determined and used as measurements of the protein's metabolism and physiology. Also, modeling may be performed on the data to fit multiple compartment models to estimate transfer between compartments. Of course, the type of mathematical modeling chosen will depend on the individual protein synthetic and clearance parameters (e.g., one-pool, multiple pools, steady state, non-steady-state, compartmental modeling, etc.). As used herein, "steady state" refers to a state during which there is insignificant change in the measured parameter over a specified period of time.

Stable isotope kinetic labeling (SILK) methodology has been shown to detect metabolic incorporation of stable (non-radioactive) isotopes into newly synthesized proteins in the cerebrospinal fluid of living subject. For detailed information regarding SILK, see U.S. Pub. Nos. 2008/0145941 and 2009/0142766, and International PCT Pub. No. WO 2006/107814, the entire content of each of which is incorporated herein by reference). SILK makes it possible to measure the production and clearance rates of proteins in the central nervous system. Thus far, this methodology has been applied to measuring the production and clearance of the amyloid beta protein (Aβ) implicated in Alzheimer's disease (AD).

However, until now, the current version of the SILK assay measures only the metabolism of total Aβ since the assay measures incorporation of a "label" (i.e., an amino acid or biomolecule which contain atoms with a different isotopic composition than what is found in nature) into the 17-28 peptide of Aβ. Such an assay allows for the measurement of the biologic activity of Aβ production inhibitors but not any type of drugs or other compounds that modulate the Aβ isoform production including, for example, gamma-secretase modulators (GSMs). As such, while Aβ is provided as an example in this embodiment, it should be understood that the methods provided herein may apply to any protein that includes isoforms (e.g., Tau).

Accordingly, in one aspect, Aβ is isolated from the biologic samples by immunoprecipitation using an antibody that recognizes either the central domain of or the N-terminal domain of Aβ. In this embodiment, the isolated peptides are eluted from the antibody, for example by using formic acid and then digested with trypsin or another protease. Contrary to the original version of the SILK-Aβ™ assay, which relies on quantitation of the 17-28 tryptic fragment of Aβ, see Table 1, the invention expands on the assay to measure the specific metabolism of the different Aβ isoforms by measuring labeled ratios in the 29-x peptides. Thus, by using an antibody that is not isoform specific, it is possible to isolate all of the C-terminal isoforms of Aβ from a biological sample. The Aβ 29-x peptides contain one leucine and can be quantified by the SILK assay using $^{13}C_6$ leucine labeling, as described herein.

The term "antibody" as used in this invention is meant to include intact molecules of polyclonal or monoclonal antibodies, as well as fragments thereof, such as Fab and F(ab')$_2$, Fv and SCA fragments which are capable of binding an epitopic determinant. The term "specifically binds" or "specifically interacts," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less.

Accordingly, the production of protein is typically based upon the rate of increase of the labeled/unlabeled protein ratio over time (i.e., the slope, the exponential fit curve, or a compartmental model fit defines the rate of protein production). For these calculations, a minimum of one sample is typically required (one could estimate the baseline label), two are preferred, and multiple samples are more preferred to calculate an accurate curve of the uptake of the label into the protein (i.e., the production rate). If multiple samples are used or preferred, the samples need not be taken from the same subject. For instance, proteins may be labeled in five different subjects at time point zero, and then a single sample taken from each subject at a different time point post-labeling.

Conversely, after the administration of labeled amino acid is terminated, the rate of decrease of the ratio of labeled to unlabeled protein typically reflects the clearance rate of that protein. For these calculations, a minimum of one sample is typically required (one could estimate the baseline label), two are preferred, and multiple samples are more preferred to calculate an accurate curve of the decrease of the label from the protein over time (i.e., the clearance rate). If multiple samples are used or preferred, the samples need not be taken from the same subject. For instance, proteins may be labeled in five different subjects at time point zero, and then a single sample taken from each subject at a different time point post-labeling. The amount of labeled protein in a CNS sample at a given time reflects the production rate or the clearance rate (i.e., removal or destruction) and is usually expressed as percent per hour or the mass/time (e.g., mg/hr) of the protein in the subject.

Combined with stable isotope labeling kinetics (SILK) for measuring the ratio of labeled biomolecules at different time points after infusion with a labeled moiety, the methodology presented herein allows for the calculation of absolute concentration of newly synthesized biomolecules (e.g., peptides or proteins) and/or the absolute concentration of each of the isoforms of that biomolecule.

The method of the invention may be used to diagnose or monitor the progression of a neurological or neurodegenerative disease by measuring the in vivo concentration of one or more biomolecules of interest in a subject. Additionally, the methods of the invention may be used to monitor the treatment of a neurological or neurodegenerative disease by measuring the in vivo concentration of a biomolecule of interest in a subject. The concentration of the biomolecule may be linked to a neurological or neurodegenerative disease such that any increase or decrease may be indicative of the presence or progression of the disease. Thus, the calculated concentration of one or more biomolecules of interest may be compared to the concentration of the same biomolecules in a corresponding normal sample, to the concentration of the same biomolecules in a subject of known neurological or neurodegenerative disease state, to the concentration of the same biomolecules from the same subject determined at an earlier time, or any combination thereof.

In addition, such methods may help identify an individual as having a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the disease.

As used herein a "corresponding normal sample" refers to a sample from the same organ and/or of the same type as the sample being examined. In one aspect, the corresponding normal sample comprises a sample of cells obtained from a healthy individual. Such a corresponding normal sample can, but need not be, from an individual that is age-matched and/or of the same sex as the individual providing the sample being examined. In another aspect, the corresponding normal sample comprises a sample of cells obtained from an otherwise healthy portion of tissue of the subject from which the sample being tested is obtained.

Reference to the concentration of biomolecules in a subject of known neurological or neurodegenerative disease state includes a predetermined concentration of a biomolecule linked to a neurological or neurodegenerative disease. Thus, the concentration may be compared to a known concentration of biomolecules obtained from a sample of a single individual or may be from an established cell line of the same type as that of the subject. In one aspect, the established cell line can be one of a panel of such cell lines, wherein the panel can include different cell lines of the same type of disease and/or different cell lines of different diseases associated with the same biomolecule. Such a panel of cell lines can be useful, for example, to practice the present method when only a small number of cells can be obtained from the subject to be treated, thus providing a surrogate sample of the subject's cells, and also can be useful to include as control samples in practicing the present methods.

Exemplary neurological or neurodegenerative diseases that may be linked to the concentration ranges of biomolecules of interest include, but are not limited to, Alzheimer's Disease, Pick's Disease, Parkinson's Disease, stroke, frontal temporal dementias (FTDs), Huntington's Disease, progressive supranuclear palsy (PSP), corticobasal degeneration (CBD), aging-related disorders and dementias, Multiple Sclerosis, Prion Diseases (e.g., Creutzfeldt-Jakob Disease, bovine spongiform encephalopathy or Mad Cow Disease, and scrapie), Lewy Body Disease, schizophrenia, Amyotrophic Lateral Sclerosis (ALS or Lou Gehrig's Disease) or other motor neuron diseases, restless legs syndrome, epilepsy or other seizure disorders, tremors, depression, mania, anxiety disorders, brain trauma or injury, narcolepsy, insomnia or other sleep disorders, autism, normal pressure hydrocephalus, pain disorders or syndromes, migraines, cluster headaches or other forms of headache, spinocerebellar disorders, muscular dystrophies, myasthenia gravis, retinitis pigmentosa or other forms of retinal degeneration. It is also envisioned that the method of the invention may be used to study the normal physiology, metabolism, and function of the CNS.

In another aspect, the present invention provides a method for assessing whether a therapeutic agent used to treat a neurological or neurodegenerative disease affects the concentration of a biomolecule of interest in the subject. For example, the concentration of the biomolecule may be measured to determine if a given therapeutic agent results in an increase, or a decrease in the concentration of the biomolecule. In one embodiment, the method is performed in vivo, as herein described. In another embodiment, the method is performed in vitro utilizing a culture of cells, where the culture of cells is the "subject" in the methods described herein. Accordingly, use of the methods provided herein will allow those of skill in the art to accurately determine the degree of change in the concentration of the biomolecule of interest, and correlate these measurements with the clinical outcome of the disease modifying treatment. Results from this aspect of the invention, therefore, may help determine the optimal doses and frequency of doses of a therapeutic agent, may assist in the decision-making regarding the design of clinical trials, and may ultimately accelerate validation of effective therapeutic agents for the treatment of neurological or neurodegenerative diseases.

Thus, the method of the invention may be used to predict which subjects will respond to a particular therapeutic agent. For example, subjects with increased concentrations of a particular biomolecule may respond to a particular therapeutic agent differently than subjects with decreased concentrations of the biomolecule. In particular, results from the method may be used to select the appropriate treatment (e.g., an agent that blocks the production of the biomolecule or an agent that increases the clearance of the biomolecule) for a particular subject. Similarly, results from the method may be used to select the appropriate treatment for a subject having a particular genotype.

The method for predicting which subjects will respond to a particular therapeutic agent include administering a therapeutic agent and a labeled moiety to the subject, wherein the labeled moiety is incorporated into the biomolecule as it is produced in the subject. In one embodiment, the therapeutic agent may be administered to the subject prior to the administration of the labeled moiety. In another embodiment, the labeled moiety may be administered to the subject prior to the administration of the therapeutic agent. The period of time between the administration of each may be several minutes, an hour, several hours, or many hours. In still another embodiment, the therapeutic agent and the labeled moiety may be administered simultaneously. The method further includes collecting at least one biological sample, which includes labeled and unlabeled biomolecules, determining a ratio of the labeled biomolecule and unlabeled biomolecule in the sample, and calculating the concentration of the unlabeled biomolecule in the subject. Thereafter, a comparison of the calculated concentration to a control value will determine whether the therapeutic agent alters the concentration (e.g., by altering the rate of production or the rate of clearance) of the biomolecule in the subject.

Those of skill in the art will appreciate that the therapeutic agent can and will vary depending upon the neurological or neurodegenerative disease or disorder to be treated and/or the biomolecule whose metabolism is being analyzed. In embodiments in which the biomolecule is A$\beta$, non-limiting examples of suitable therapeutic agents include gamma-secretase inhibitors, beta-secretase inhibitors, alpha-secretase activators, RAGE inhibitors, small molecule inhibitors of A$\beta$ or A$\beta$ production, humanized antibodies against A$\beta$, A$\beta$ CNS clearance activators, small molecule inhibitors of A$\beta$ polymerization, platinum-based inhibitors of A$\beta$ production, platinum-based inhibitors of polymerization, agents that interfere with metalprotein interactions, proteins (such as, e.g., low-density lipoprotein receptor-related protein (LRP) or soluble LRP) that bind soluble A$\beta$, and antibodies that clear soluble A$\beta$ and/or break down deposited A$\beta$. Other suitable AD therapeutic agents include cholesterylester transfer protein (CETP) inhibitors, metalloprotease inhibitors, cholinesterase inhibitors, NMDA receptor antagonists, hormones, neuroprotective agents, and cell death inhibitors. Many of the above mentioned therapeutic agents may also affect the in vivo metabolism of other proteins implicated in neurodegenerative disorders. Additional therapeutic agents that may affect the metabolism of tau, for example, include tau kinase inhibitors, tau aggregation inhibitors, cathepsin D inhibitors, etc. Furthermore, therapeutic agents that may affect the in vivo metabolism of synuclein include sirtuin 2 inhibitors, synuclein aggregation inhibitors, proteosome inhibitors, etc.

The therapeutic agent may be administered to the subject in accordance with known methods. Typically, the therapeutic agent will be administered orally, but other routes of administration such as parenteral or topical may also be used. The amount of therapeutic agent that is administered to the subject can and will vary depending upon the type of agent, the subject, and the particular mode of administration. Those skilled in the art will appreciate that dosages may be determined with guidance from Goodman & Goldman's The Pharmacological Basis of Therapeutics, Tenth Edition (2001), Appendix II, pp. 475-493, and the Physicians' Desk Reference.

It should be understood that the methods of the invention described herein can be adapted to a high throughput format, thus allowing the examination of a plurality (i.e., 2, 3, 4, or more) of samples and/or biomolecules, which independently can be the same or different, in parallel. A high throughput format provides numerous advantages. For example, a high throughput format allows for the examination/quantitation of two, three, four, etc., different biomolecules, alone or in combination, of a subject. Finally, a high throughput format allows, for example, control samples (positive controls and or negative controls) to be run in parallel with test samples. In addition a high throughput method may allow immunoprecipitation of multiple proteins at the same time using multiple antibodies.

In another aspect, the invention provides a kit for performing the methods of the invention. In one embodiment, a kit is provided for diagnosing and/or monitoring the progression or treatment of a neurological or neurodegenerative disease in a subject. The kit includes one or more labeled moieties (e.g., labeled amino acids) and a means for administering the one or more amino acids to the subject. The kit may further include a means for obtaining a biological sample at regular time intervals from the subject. In certain embodiments, the kit will also include instructions for detecting and determining the ratio of labeled to unlabeled biomolecules of interest over time and for calculating the concentration of the unlabeled biomolecule. In one embodiment, the instructions will disclose methods for comparing the calculated concentration to certain standards and/or controls as disclosed herein.

In another embodiment, the kit of the invention provides a compartmentalized carrier including one or more containers containing the labeled moiety and the various means for performing the methods of the invention.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Stable Isotope Kinetic Labeling

This example illustrates the improvements developed over the SILK methodology. A cell culture media was generated with a known ratio of labeled to unlabeled Aβ. This standard curve media was thereafter used to test the detection and quantitation of the 29-x peptides of Aβ. Using this media, a series of tests were performed to improve the solubility of the 29-x peptides as well as to establish improved chromatography conditions in order to increase detection of the peptides.

Increased Solubility of the 29-x Peptides—

The original SILK-Aβ™ methodology was modified by use of 0.025% of detergent, for example Tween-20, Triton, or CHAPS, instead of using 0.5M guanidine for the IP and washing steps. The peptides are kept in the 0.025% detergent solution during digestion as well and until injected into the mass spectrometer. Aβ is a very hydrophobic peptide and the addition of Tween-20 greatly improves the solubility and mass spectrometer signal from the 29-x peptides to the point where ion intensities of the 29-40 that are as high as for the 17-28 peptide are attainable. This is significant because Aβ 40 is the most abundant Aβ species and thus most of the 17-28 peptide arises from the Aβ 40 peptide. As such, having the ion intensities of the two peptides being similar suggests that all of the Aβ 29-40 is in solution for detection by the mass spectrometer.

Maintaining the 29-x Peptides in the Reduced State—

In addition methods were developed for keeping the 29-x peptides in the reduced state. For example, these peptides contain one methionine residue which can be oxidized. In one exemplary characterization, it was found that approximately 10% of the methionine is oxidized in CSF and media, so by adding a reducing agent it was possible to eliminate the oxidized form and increase the signal by 10% or greater, depending on the oxidation state originally present in the biological sample. This oxidation state could vary—specifically with disease states such as Alzheimer's disease which is known to be accompanied by oxidative damage. Reducing agents, such as beta-mercaptoethanol and tris(2-carboxyethyl)phosphine hydrochloride (TCEP), are used to eliminate methionine oxidation.

Modification of the Column—

Finally, to avoid having the Aβ peptides stick to the columns, the C18 column was swapped for a C1 column. A column having much lower carbon content than that of the C18, such as a C1, C4 or C8 column, is much less hydrophobic, allowing for greater recovery of the Aβ peptides, improving the peak shape of the peptides, as well as potentially reducing carryover between sample runs.

Figure 2:
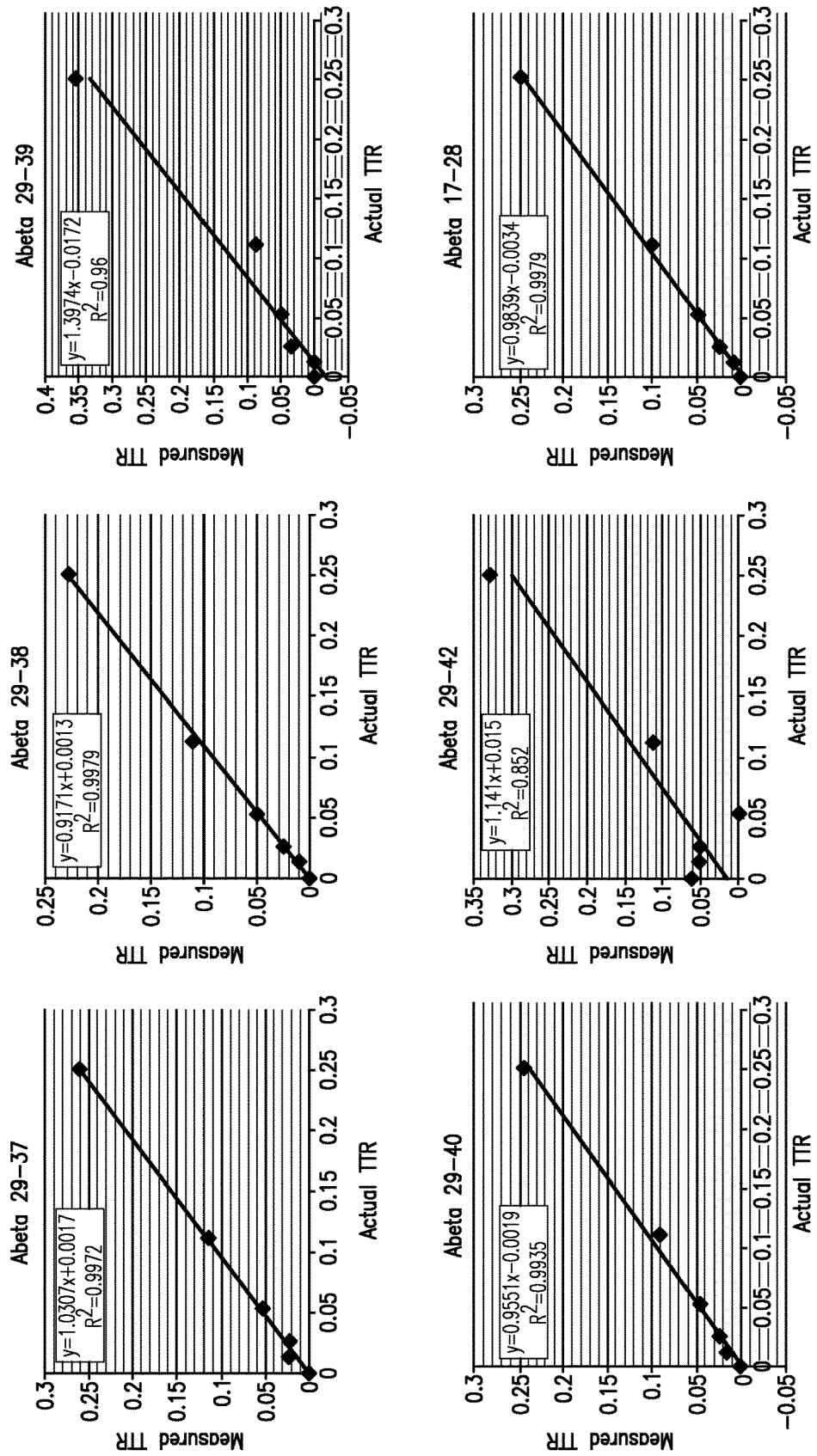
FIG. 2 is a graphical representation showing standard curves from media. The labeling ratios were analyzed for each of the different Aβ (Abeta) 29-x isoforms, as well as the 17-28 peptide, in media with different percentage labeling. TTR represents the tracer to tracee ratio.

As shown in FIG. 1, the methods provided herein are able to detect all of the 29-x peptides, as well as the 17-28 peptide in cell culture media. In addition to observing the peaks, studies have been performed to determine if the peaks from these peptides can be reliably quantitated, thereby generating standard curves for the C-terminal isoforms. Using the standard curve media provided the ability to quantitate the isoforms (see FIG. 2).

EXAMPLE 2

Quantitation Standard

This example demonstrates that spiking of quantitation standard can be used for calculation of the ratio between endogenous peptides and spiked peptides. Thus, spiking in known amounts of labeled Aβ 37, Aβ 38, Aβ 39, Aβ 40 and Aβ 42 allows specific quantitation of those isoforms in addition to quantitation of the total Aβ concentration in the sample.

Figure 3:
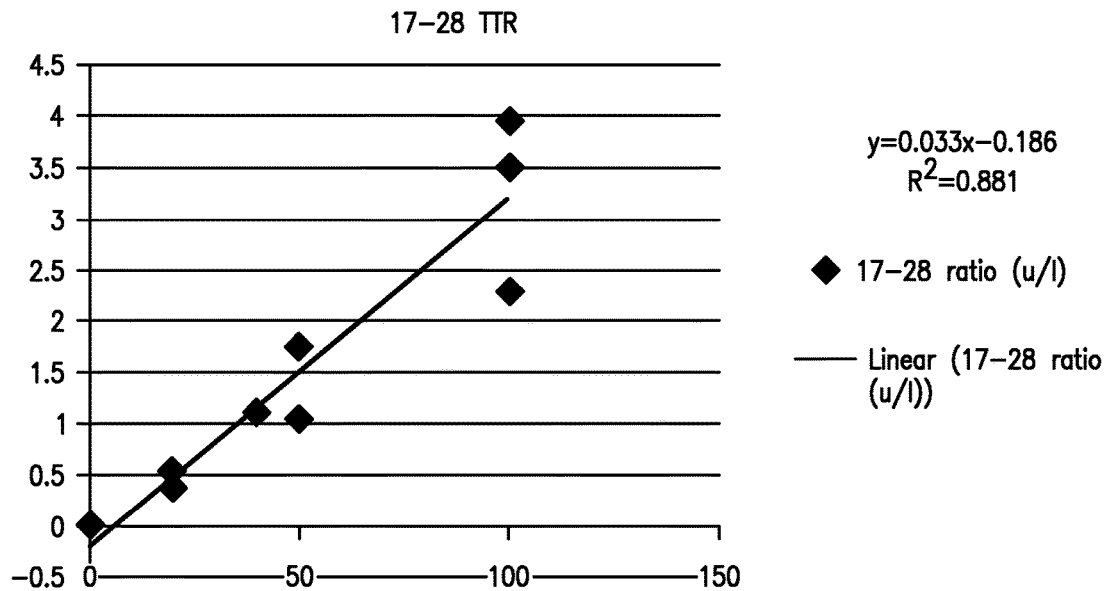
FIGS. 3 and 4 are graphical diagrams showing that a Quantitation Standard can be used for calculating the ratio between endogenous peptides and spiked peptides.
Figure 4:
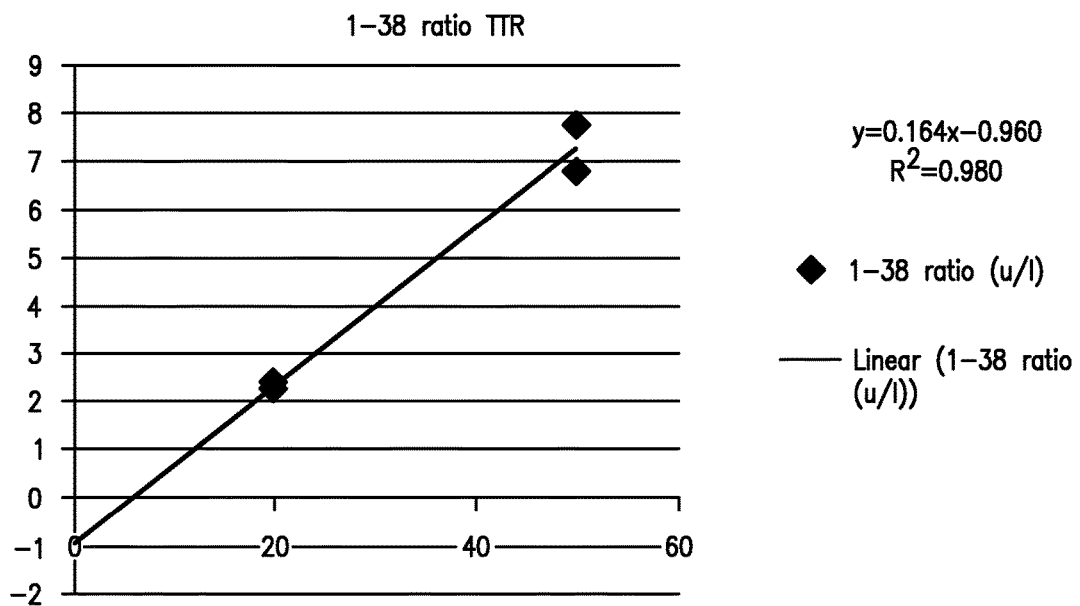

Due to the lead time of manufacturing labeled peptides we originally used unlabeled peptides as the spike in and used media from cells grown in 100% $^{13}C_6$ leucine as the unknown. We spiked in unlabeled Aβ 38 and Aβ 42 into 100% $^{13}C_6$ leucine media and measured the ratios. As more unlabeled peptide was spiked into the media the tracer to tracee ratio (TTR, in this experiment defined as ratio of unlabeled to labeled) of both the 17-28 peptide and the 29-38 peptide increased linearly. (See FIGS. 3 and 4).

This illustrates the feasibility of measuring the concentration of these peptides based upon spiking a standard into a solution containing unknown amounts of peptide which contains a distinct isotopic labeling signature.

EXAMPLE 3

Quantitation Standard to Calculate Absolute Concentration

This example demonstrates use of the Quantitation Standard to calculate the production or clearance rates of biomolecules of interest, which is used to calculate absolute concentration of those biomolecules.

A sample containing Aβ or other peptide isoforms (including, but not limited to Aβ 1-37, Aβ 1-38, Aβ 1-39, Aβ 1-40, Aβ 1-42) in both unlabeled form, as well as labeled with $^{13}C_6$-leucines (the labeled leucine is incorporated into the sample by the subject's natural biological processes) is spiked with Quantitation Standard. The ratio of labeled to unlabeled peptide over time is used to calculate kinetic production and clearance rates (metabolism) of the peptide in the subject. The ratios of labeled or unlabeled peptide to Quantitation Standard are used to calculate concentrations of the respective versions of the peptide.

The biomolecule (e.g., protein or peptide) is immunoprecipitated utilizing an antibody specific to the protein. For Aβ, the immunoprecipitation takes place in 25 mM ammonium bicarbonate, pH 7.6, with 0.025% Tween-20 added during each step of the Aβ isolation and preparation. For Aβ, the sample is incubated with the antibody for 2-3 hours at room temperature, washed three times and eluted from the antibody by the addition of 50 μl of formic acid and speed-vac'ed to dryness. The sample is reconstituted in 20 μl of in 25 mM ammonium bicarbonate, 10% acetonitrile, pH 7.6, with 0.025% Tween-20 added and digested with 20 μl of trypsin or another endoprotease overnight. After digestion, 10 of 1% beta-mercaptoethanol is added to reduce oxidation of the methionine residue.

For analysis, 5 μl of the sample is injected onto a BioBasic C18 column or other reverse phase or protein separation column for separation of the peptides before injection into the mass spectrometer. The m/z ratio of each C-terminus tryptic peptide corresponding to, but not limited to isoforms 17-28, and 29-37, 29-38, 29-39, 29-40 and 29-42 are then scanned for and selected for CID (done for all unlabeled, +6D labeled and +12D labeled (Quantitation Standard)). This results in the $ms^2$ data utilized to perform the quantitation. XCalibur processing software is then utilized to calculate total peak areas of all $ms^2$ data for the unlabeled, +6D labeled and +12D labeled.

Quantitation of production and clearance rates and absolute concentration are then calculated utilizing two sets of standard curves run concurrently with the biological samples. The first standard curve contains Aβ peptides labeled with known ratios of +6D leucine to unlabeled leucine (from 0-25%). This standard curve is analyzed by linear regression and the ratio of peak areas for unlabeled and +6D labeled peptides from the biological source is normalized based on the standard curve linear regression.

The second standard curve consists of known quantities of synthetic or biologically generated standard. Each species to be quantified must be present in the curve—e.g., if wanting to measure concentration of unlabeled and $^{13}C_6$ labeled Aβ 17-28 both $^{13}C_6$ labeled and unlabeled Aβ must be present in the standard curve. In addition this standard curve contains the Quantitation Standard—for Aβ 1-40, a peptide containing two $^{13}C_6$ phenylalanines in positions 19 and 20 (part of the 17-28 peptide) and two $^{13}C_6$ isoleucines in position 31 and 32 (part of the 29-x peptide) was used; in addition a $^{15}N$ peptide could be used or a combination of other amino acids that will give a m/z signature that is distinct from the unlabeled and the metabolically labeled peptides. All of these peptides are spiked into a matrix resembling the endogenous matrix and processed as if they came from a subject (immunoprecipitation, digestion, mass spectrometry analysis). The peak areas of the unlabeled, +6 and +12D labeled peptides are again calculated by XCalibur processing software, standard curves plotted, and linear regression determined. The areas for the endogenous peptides are calculated as done previously. The areas for the unlabeled and +6D endogenously labeled peptides are added together and compared to the standard curve of the +12D synthetic standards and the areas calculated from the linear regression. In this manner the total amount of endogenous peptide are directly compared to a known quantity of internal synthetic standards, thus unambiguously determining the absolute concentration of Aβ present in each biological sample. In addition, concentration of each of the unlabeled or $^{13}C_6$ labeled peptides can be calculated individually.

EXAMPLE 4

Multiple Runs of Samples with Standard Curve

This Example demonstrates a variation of the methodology set forth in Example 3. 20 ng of Aβ quantitation standard was spiked into media samples that already contained both unlabeled and metabolically ($^{13}C_6$ leucine) labeled Aβ.

The quantitation standard used was Aβ 1-40 containing 2 $^{13}C_6$ phenylalanine at position 19 and 20 (F* in table below, part of the 17-28 peptide) and 2 $^{13}C_6$ isoleucines in position 31 and 32 (I* in the table below, part of the 29-x peptide).

TABLE 2

Showing the location of the labeled amino acids in the Aβ 40 peptide. Similar peptides can be created for Aβ 1-37, 1-38, 1-39, 1-40, 1-42.

| Aβ 40 | DAEFR_HDSGYEVHHQK_LVF*F*AEDVGSNK_GAI*I*GLMIVGGVV | SEQ ID NO: 4 |
|---|---|---|

Samples were digested with trypsin to yield the 17-28 peptide as well as the 29-x peptides.

The media samples come from individual cell culture experiments and thus have different amounts of Aβ in them due to biological variation.

For each run a quantitation curve was run which contained unlabeled Aβ ranging from 0.4 ng/mL to 100 ng/mL. Quantitation standard was spiked into the quantitation before performing. IP on the samples.

Figure 5:
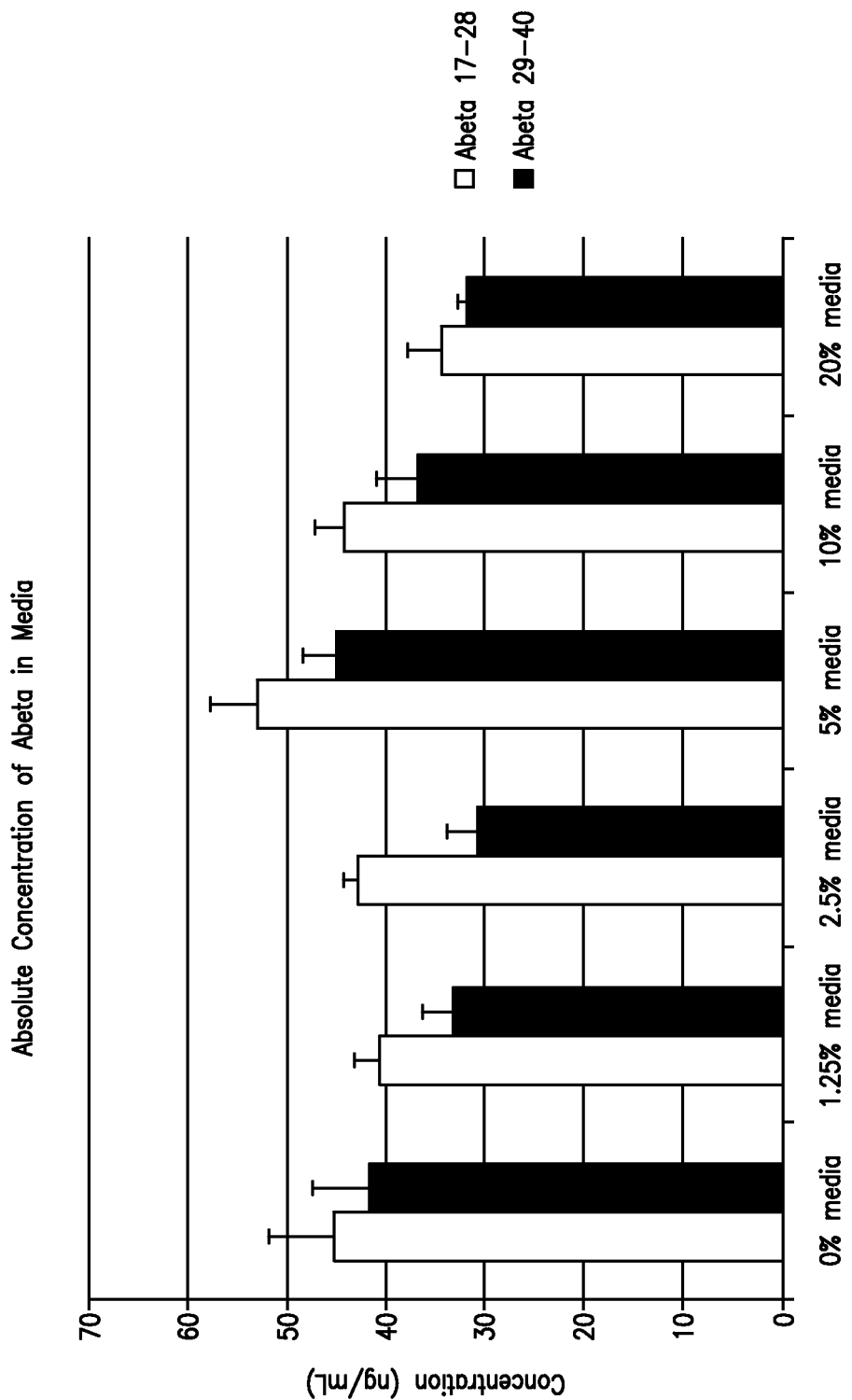
FIG. 5 is a graphical diagram showing the absolute concentration of Aβ (Abeta) as measured in media samples from cells secreting Aβ.

The ratio between unlabeled ions and ions originating from the quantitation standard was used in conjunction with the quantitation standard curve to calculate the amount of unlabeled Aβ 17-28 as well as Aβ 29-40 in each sample. Data shown in Table 2 is average of 3 runs of the samples (see FIG. 5).

|  | Abeta 17-28 | Stdev | CV | Abeta 29-40 | Stdev | CV |
| --- | --- | --- | --- | --- | --- | --- |
| 0% media | 45.28868 | 6.574515 | 15% | 41.66965 | 5.56925 | 13% |
| 1.25% media | 40.49848 | 2.621899 | 6% | 33.13193 | 3.268642 | 10% |
| 2.5% media | 42.88804 | 1.208532 | 3% | 30.63681 | 3.207314 | 10% |
| 5% media | 53.13186 | 4.508435 | 8% | 44.93799 | 3.229995 | 7% |
| 10% media | 44.13336 | 2.942345 | 7% | 36.77698 | 4.169602 | 11% |
| 20% media | 34.50198 | 3.176109 | 9% | 31.86353 | 0.88997 | 3% |

Although the invention has been described with reference to the above example, it will be understood that modifications and variations are encompassed within the spirit and scope of the invention. Accordingly, the invention is limited only by the following claims.

What is claimed is:

1. A method of determining the absolute concentration of an amyloid-beta protein (Aβ), isoform, variant or digestion product thereof in a subject, comprising:
   (a) metabolically labeling the endogenous Aβ protein isoform, variant or digestion product thereof by administering at least one labeled moiety to the subject, wherein the at least one labeled moiety metabolically incorporates into the endogenous Aβ protein isoform, variant or digestion product thereof;
   (b) contacting a biological sample obtained from the subject with a Quantitation Standard (QS) comprising a known concentration of a biomolecule labeled with two labeled moieties such that the labeled QS has a molecular weight that differs from the metabolically labeled endogenous Aβ protein isoform, variant or digestion product thereof, wherein the QS is an Aβ peptide, wherein the biological sample comprises a metabolically labeled fraction of the endogenous Aβ protein isoform, variant or digestion product thereof and an unlabeled fraction of the Aβ protein, isoform, variant or digestion product thereof;
   (c) isolating the metabolically labeled, the unlabeled and the labeled QS forms of Aβ protein isoform, variant or digestion product thereof from the biological sample using a detergent to increase the labeled Aβ, unlabeled Aβ peptides and QS solubility;
   (d) maintaining the labeled Aβ, unlabeled Aβ peptides and QS in a reduced state to increase said peptides detection;
   (e) subjecting the labeled Aβ, unlabeled Aβ peptides and QS to mass spectroscopy analysis; and
   (f) calculating the absolute concentration of the endogenous, metabolically labeled and unlabeled, Aβ protein isoform, variant or digestion product thereof using the known concentration of Aβ protein isoform, variant or digestion product in the labeled QS.

2. The method of claim 1, wherein the subject is a human, animal or a culture of cells.

3. The method of claim 1, wherein the two labeled moieties comprise a non-radioactive isotope that is selected from the group consisting of $^{2}H$, $^{13}C$, $^{15}N$, $^{17}O$, $^{18}O$, $^{33}S$, $^{34}S$, and $^{36}S$.

4. The method of claim 1, wherein the endogenous amyloid-beta protein (Aβ), isoform, variant or digestion product thereof is labeled with a labeled amino acid.

5. The method of claim 1, further comprising comparing the concentration of the unlabeled endogenous amyloid-beta protein (Aβ), isoform, variant or digestion product thereof to the concentration of the same biomolecule in a corresponding normal sample, to the concentration of the same biomolecule in a subject of known neurological or neurodegenerative disease state, to the concentration of the same biomolecule from the same subject determined at an earlier time, or any combination thereof.

6. The method of claim 5, wherein the neurological or neurodegenerative disease is selected from the group consisting of Alzheimer's Disease, Parkinson's Disease, stroke, frontal temporal dementias (FTDs), Huntington's Disease, progressive supranuclear palsy (PSP), corticobasal degeneration (CBD), aging-related disorders and dementias, Multiple Sclerosis, Prion Diseases, Lewy Body Disease, Pick's Disease, motor neuron diseases, restless leg syndrome, seizure disorders, tremors, depression, mania, anxiety disorders, brain trauma or injury, narcolepsy, sleep disorders, autism, normal pressure hydrocephalus, pain disorders or syndromes, migraines, headaches, spinocerebellar disorders, muscular dystrophies, myasthenia gravis, retinal degeneration, and Amyotrophic Lateral Sclerosis.

7. The method of claim 1, wherein the method further comprises determining a ratio of the labeled endogenous amyloid-beta protein (Aβ), isoform, variant or digestion product thereof in the sample to the QS (labeled:QS) and determining a ratio of the unlabeled endogenous amyloid-beta protein (Aβ), isoform, variant or digestion product thereof in the sample to the QS (unlabeled:QS).

8. The method of claim 7, wherein calculating the concentration of the unlabeled endogenous biomolecule comprises multiplying the concentration of the Quantitation Standard with the determined ratio of unlabeled endogenous biomolecule to the Quantitation Standard.

9. The method of claim 7, wherein calculating the concentration of the labeled endogenous biomolecule comprises multiplying the concentration of the Quantitation Standard with the determined ratio of labeled endogenous biomolecule to the Quantitation Standard.

10. The method of claim 4, wherein the labeled amino acid and the Quantitation Standard are independently labeled with a non-radioactive isotope selected from the group consisting of $^{2}H$, $^{13}C$, $^{15}N$, $^{17}O$, $^{18}O$, $^{33}S$, $^{34}S$, and $^{36}S$.

11. The method of claim 10, wherein the labeled amino acid is an essential amino acid.

12. The method of claim 1, wherein the sample is selected from the group consisting of cerebral spinal fluid (CSF), blood, plasma, urine, saliva spinal cord tissue, brain tissue and tears.

13. The method of claim 7, further comprising comparing the concentration of the unlabeled endogenous amyloid-beta protein (Aβ), isoform, variant or digestion product thereof to the concentration of the same biomolecule in a corresponding normal sample, to the concentration of the same biomolecule in a subject of known neurological or neurodegenerative disease state, to the concentration of the same biomolecule from the same subject determined at an earlier time, or any combination thereof.

14. The method of claim 13, wherein the neurological or neurodegenerative disease is selected from the group consisting of Alzheimer's Disease, Parkinson's Disease, stroke, frontal temporal dementias (FTDs), Huntington's Disease, progressive supranuclear palsy (PSP), corticobasal degeneration (CBD), aging-related disorders and dementias, Multiple Sclerosis, Prion Diseases, Lewy Body Disease, Pick's Disease, motor neuron diseases, restless leg syndrome, seizure disorders, tremors, depression, mania, anxiety disorders, brain trauma or injury, narcolepsy, sleep disorders, autism, normal pressure hydrocephalus, pain disorders or syndromes, migraines, headaches, spinocerebellar disorders, muscular dystrophies, myasthenia gravis, retinal degeneration, and Amyotrophic Lateral Sclerosis.

15. The method of claim 1, wherein the biomolecule is selected from the group consisting of Aβ 1-37, Aβ 1-38, Aβ 1-39, Aβ 1-40, Aβ 1-41, Aβ 1-42, and Aβ 1-43.

16. The method of claim 1, wherein the subject is a human.

17. The method of claim 7, wherein calculating the concentration of the unlabeled endogenous amyloid-beta protein (Aβ), isoform, variant or digestion product thereof comprises multiplying the known concentration of the Quantitation Standard with the ratio of labeled to unlabeled endogenous amyloid-beta protein (Aβ), isoform, variant or digestion product thereof in the sample.

* * * * *

SEQUENCE LISTING

<160> NUMBER OF SEQ ID NOS: 5

<210> SEQ ID NO 1
<211> LENGTH: 37
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly
        35

<210> SEQ ID NO 2
<211> LENGTH: 38
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 3
<211> LENGTH: 39
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35

<210> SEQ ID NO 4
<211> LENGTH: 40
<212> TYPE: PRT
<213> ORGANISM: Homo sapiens

<400> SEQUENCE: 4

-continued

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35              40

<210> SEQ ID NO 5
<211> LENGTH: 42
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35              40
```